United States Patent
Geng et al.

(10) Patent No.: US 10,351,848 B2
(45) Date of Patent: Jul. 16, 2019

(54) METHOD FOR CONSTRUCTING NUCLEIC ACID SINGLE-STRANDED CYCLIC LIBRARY AND REAGENTS THEREOF

(71) Applicant: MGI TECH CO., LTD., Shenzhen (CN)

(72) Inventors: Chunyu Geng, Shenzhen (CN); Ruoying Chen, Shenzhen (CN); Yuan Jiang, Shenzhen (CN); Xia Zhao, Shenzhen (CN); Rongrong Guo, Shenzhen (CN); Lingyu He, Shenzhen (CN); Yaqiao Li, Shenzhen (CN); Wenwei Zhang, Shenzhen (CN); Hui Jiang, Shenzhen (CN); Radoje Drmanac, Los Altos Hill, CA (US)

(73) Assignee: MGI TECH CO., LTD., Shenzhen (CN)

( * ) Notice: Subject to any disclaimer, the term of this patent is extended or adjusted under 35 U.S.C. 154(b) by 113 days.

(21) Appl. No.: 15/510,882

(22) PCT Filed: Nov. 26, 2014

(86) PCT No.: PCT/CN2014/092294
§ 371 (c)(1),
(2) Date: Mar. 13, 2017

(87) PCT Pub. No.: WO2016/037418
PCT Pub. Date: Mar. 17, 2016

(65) Prior Publication Data
US 2018/0291371 A1     Oct. 11, 2018

Related U.S. Application Data

(63) Continuation-in-part of application No. PCT/CN2014/086421, filed on Sep. 12, 2014.

(51) Int. Cl.
*C12N 15/10* (2006.01)
*C12Q 1/6806* (2018.01)
(Continued)

(52) U.S. Cl.
CPC ....... *C12N 15/1093* (2013.01); *C12Q 1/6806* (2013.01); *C12Q 1/6853* (2013.01);
(Continued)

(58) Field of Classification Search
CPC ............. C12N 15/1093; C12Q 1/6855; C12Q 1/6853; C12Q 1/6806
See application file for complete search history.

(56) References Cited

U.S. PATENT DOCUMENTS

2010/0120098 A1* 5/2010 Grunenwald .......... C12N 15/10
435/91.2

FOREIGN PATENT DOCUMENTS

| CN | 1940088 A | 4/2007 |
| CN | 102016068 | 4/2011 |

(Continued)

OTHER PUBLICATIONS

Datasheet for User(TM) Enzyme by NEB (Year: 2013).*
(Continued)

*Primary Examiner* — Jeremy C Flinders
(74) *Attorney, Agent, or Firm* — Westman, Champlin & Koehler, P. A.; Z. Peter Sawicki

(57) ABSTRACT

Provided are a method for constructing a nucleic acid single-stranded cyclic library and the reagents used therein. By the combination of interruption via a transposase with a restricted nick translation reaction, the method realizes a simple and rapid nucleic acid single-stranded cyclic library construction.

10 Claims, 3 Drawing Sheets
Specification includes a Sequence Listing.

(51) Int. Cl.
    *C12Q 1/6853* (2018.01)
    *C12Q 1/6855* (2018.01)
    *C12N 15/66* (2006.01)

(52) U.S. Cl.
    CPC ........ *C12Q 1/6855* (2013.01); *C12N 15/1089* (2013.01); *C12N 15/66* (2013.01); *C12Q 2525/191* (2013.01)

(56) References Cited

FOREIGN PATENT DOCUMENTS

| CN | 102102130 | | 6/2011 |
|---|---|---|---|
| CN | 102181943 | | 9/2011 |
| CN | 102286632 | A | 12/2011 |
| CN | 103710323 | A | 4/2014 |
| WO | 0138573 | A1 | 5/2001 |
| WO | 0138574 | A1 | 5/2001 |

OTHER PUBLICATIONS

Mathew C.G.P. (1984) Radiolabeling of DNA by Nick Translation. In: Walker J.M. (eds) Nucleic Acids. Methods in Molecular Biology, vol. 2. Humana Press (Year: 1984).*
International Search Report issued for PCT/CN2014/092294, dated Jul. 2, 2015.
Written Opinion issued for PCT/CN2014/092294, dated Jul. 2, 2015.
Timothy D. Harris et al., 2008, "Single-Molecule DNA Sequencing of a Viral Genome" Science, vol. 320 ISSN: 1095-9203 pp. 106-109.
International Search Report issued for PCT/CN2014/086421, dated Jun. 18, 2015.
Written Opinion issued for PCT/CN2014/086421, dated Jun. 18, 2015.

* cited by examiner overall result of sample 1:

the number of peaks: 1 noise: 0.4 corrected area 1: 21.9 region table of Sample 1:

| start [bp] | stop [bp] | corrected area | total number % | Average fragment[bp] | CV value of fragment distribution[%] | Con. [pg/μl] | Molar Con. [pmol/l] | colour |
|---|---|---|---|---|---|---|---|---|
| 200 | 1,000 | 21.9 | 25 | 429 | 50.4 | 28.57 | 141.7 | ▨ |

| chip position | serial number of the chip | column(1) | Number of sequencing cycles |
|---|---|---|---|
| 2 | GS73029-FS3 | 1 | 20 21 24 25 26 27 28 64 65 66 67 68 |
|  |  | 2 |  |
|  |  | 3 |  |
|  |  | 4 |  |

SEQUENCE LISTING

<160> NUMBER OF SEQ ID NOS: 12

<210> SEQ ID NO 1
<211> LENGTH: 35
<212> TYPE: DNA
<213> ORGANISM: Artificial Sequence
<220> FEATURE:
<223> OTHER INFORMATION: Sequence A of adaptor No.1
<220> FEATURE:
<221> NAME/KEY: misc_feature
<222> LOCATION: (4)..(4)
<223> OTHER INFORMATION: y = uracil
<220> FEATURE:
<221> NAME/KEY: misc_feature
<222> LOCATION: (14)..(14)

<223> OTHER INFORMATION: y = uracil

<400> SEQUENCE: 1
aggycgccag cccyacagat gtgtataaga gacag                              35

<210> SEQ ID NO 2
<211> LENGTH: 19
<212> TYPE: DNA
<213> ORGANISM: Artificial Sequence
<220> FEATURE:
<223> OTHER INFORMATION: Sequence B of adaptor No.1
<220> FEATURE:
<221> NAME/KEY: modified_base
<222> LOCATION: (19)..(19)
<223> OTHER INFORMATION: dideoxy modification

<400> SEQUENCE: 2
ctgtctctta tacacatct                                               19

<210> SEQ ID NO 3
<211> LENGTH: 44
<212> TYPE: DNA
<213> ORGANISM: Artificial Sequence
<220> FEATURE:
<223> OTHER INFORMATION: Sequence A of adaptor No.2
<220> FEATURE:
<221> NAME/KEY: modified_base
<222> LOCATION: (1)..(1)
<223> OTHER INFORMATION: phosphorylation
<220> FEATURE:
<221> NAME/KEY: misc_feature
<222> LOCATION: (17)..(25)
<223> OTHER INFORMATION: n is a, c, g, or t
<220> FEATURE:
<221> NAME/KEY: modified_base
<222> LOCATION: (44)..(44)
<223> OTHER INFORMATION: dideoxy modification

<400> SEQUENCE: 3
actgctgagc tgaggannnn nnnnntcgtc aaggtcgcca gccc                    44

<210> SEQ ID NO 4
<211> LENGTH: 16
<212> TYPE: DNA
<213> ORGANISM: Artificial Sequence
<220> FEATURE:
<223> OTHER INFORMATION: Sequence B of adaptor No.2
<220> FEATURE:
<221> NAME/KEY: modified_base
<222> LOCATION: (16)..(16)
<223> OTHER INFORMATION: dideoxy modification

<400> SEQUENCE: 4
tcctcagctc agcagt                                                  16

<210> SEQ ID NO 5
<211> LENGTH: 35
<212> TYPE: DNA
<213> ORGANISM: Artificial Sequence
<220> FEATURE:
<223> OTHER INFORMATION: Primer 1
<220> FEATURE:
<221> NAME/KEY: misc_feature
<222> LOCATION: (4)..(4)
<223> OTHER INFORMATION: y = uracil
<220> FEATURE:
<221> NAME/KEY: misc_feature
<222> LOCATION: (14)..(14)
<223> OTHER INFORMATION: y = uracil

<400> SEQUENCE: 5

```
aggycgccag cccyacagat gtgtataaga gacag                              35
```

<210> SEQ ID NO 6
<211> LENGTH: 19
<212> TYPE: DNA
<213> ORGANISM: Artificial Sequence
<220> FEATURE:
<223> OTHER INFORMATION: Primer 2
<220> FEATURE:
<221> NAME/KEY: misc_feature
<222> LOCATION: (5)..(5)
<223> OTHER INFORMATION: y = uracil
<220> FEATURE:
<221> NAME/KEY: misc_feature
<222> LOCATION: (14)..(14)
<223> OTHER INFORMATION: y = uracil

<400> SEQUENCE: 6

```
gggcyggcga cctygacga                                               19
```

<210> SEQ ID NO 7
<211> LENGTH: 26
<212> TYPE: DNA
<213> ORGANISM: Artificial Sequence
<220> FEATURE:
<223> OTHER INFORMATION: third adaptor sequence-1
<220> FEATURE:
<221> NAME/KEY: modified_base
<222> LOCATION: (1)..(1)
<223> OTHER INFORMATION: phosphorylation

<400> SEQUENCE: 7

```
aagtcggagg ccaagcgtgc ttagga                                       26
```

<210> SEQ ID NO 8
<211> LENGTH: 8
<212> TYPE: DNA
<213> ORGANISM: Artificial Sequence
<220> FEATURE:
<223> OTHER INFORMATION: third adaptor sequence-2
<220> FEATURE:
<221> NAME/KEY: modified_base
<222> LOCATION: (8)..(8)
<223> OTHER INFORMATION: dideoxy modification

<400> SEQUENCE: 8

```
tccgactt                                                            8
```

<210> SEQ ID NO 9
<211> LENGTH: 22
<212> TYPE: DNA
<213> ORGANISM: Artificial Sequence
<220> FEATURE:
<223> OTHER INFORMATION: L-Oligo adaptor
<220> FEATURE:
<221> NAME/KEY: modified_base
<222> LOCATION: (1)..(1)
<223> OTHER INFORMATION: phosphorylation

<400> SEQUENCE: 9

```
catgtagtgt acgatccgac tt                                           22
```

<210> SEQ ID NO 10
<211> LENGTH: 19
<212> TYPE: DNA
<213> ORGANISM: Artificial Sequence
<220> FEATURE:
<223> OTHER INFORMATION: adaptor primer-1
<220> FEATURE:

```
<221> NAME/KEY: modified_base
<222> LOCATION: (1)..(1)
<223> OTHER INFORMATION: labeled with biotin

<400> SEQUENCE: 10
tcctaagcac gcttggcct                                             19

<210> SEQ ID NO 11
<211> LENGTH: 22
<212> TYPE: DNA
<213> ORGANISM: Artificial Sequence
<220> FEATURE:
<223> OTHER INFORMATION: adaptor primer-2
<220> FEATURE:
<221> NAME/KEY: modified_base
<222> LOCATION: (1)..(1)
<223> OTHER INFORMATION: phosphorylation

<400> SEQUENCE: 11
catgtagtgt acgatccgac tt                                         22

<210> SEQ ID NO 12
<211> LENGTH: 24
<212> TYPE: DNA
<213> ORGANISM: Artificial Sequence
<220> FEATURE:
<223> OTHER INFORMATION: fourth adaptor

<400> SEQUENCE: 12
gtacactaca tgtcctaagc acgc                                       24
```

METHOD FOR CONSTRUCTING NUCLEIC ACID SINGLE-STRANDED CYCLIC LIBRARY AND REAGENTS THEREOF

CROSS-REFERENCE TO RELATED APPLICATION

This application is the U.S. national phase of PCT Application No. PCT/CN2014/092294 filed on Nov. 26, 2014, which claims a priority to and benefits of PCT Application No. PCT/CN2014/086421, filed with the State Intellectual Property Office of P. R. China on Sep. 12, 2014, the entire contents of which are incorporated herein by reference.

FIELD

The present disclosure relates to the field of molecular biology, particular to a method and a reagent for constructing a library containing single-stranded cyclic nucleic acids.

BACKGROUND

The Next-generation sequencing has experienced a period of rapid development since Roche invented the pyrosequencing method. However, with the development of high-throughput sequencing, high-throughput and sample preparation in low-cost gradually become key considerations in the sequencing field. Sample processing methods and automated devices based on various principles have been developed, including sample fragmentation, end-repairing and adaptor ligation to the nucleic acid molecules and a final library construction.

The sample fragmentation is mainly achieved by a physical method (such as ultrasonic shearing) or an enzymatic method (i.e., using non-specific endonuclease). The physical method is dominated by Covaris instrument which is based on Adaptive Focused Acoustic (AFA) technology. Under the isothermal condition, acoustic energy in a wavelength of 1 mm is focused on a sample geometrically by a spherical solid ultrasonic sensor at >400 kHz with, thereby guaranteeing the nucleic acid sample retained integrity, and achieving high recovery. Covaris instrument includes the economical M-series, S-series with single-tube and full-power, and E and L series with higher throughput. Although fragments obtained by the physical method are in good randomness, their throughput depends on Covaris instrument with high throughput, and such fragments obtained need to be subjected to end-repairing, adaptor ligation and various purifications subsequently. The enzymatic method includes NEB Next dsDNA Fragmentase developed by NEB company. This reagent can fragment double-stranded DNAs by randomly generating nicks on the double-stranded DNAs, followed by cutting the complementary double-stranded DNA chain with an enzyme which can recognize the nick sites. Although this reagent, with a good randomness, can be used in genomic DNAs, whole genome amplification products and PCR products, some artificial insertion and deletion of short fragment will be generated, and it is also unavoidable to proceed with end-repairing, adaptor ligation, PCR and corresponding purifications. Furthermore, the transposases fragmentation kit, led by the Nextera kit from Epicentra company (purchased by Illumina), may complete DNA fragmentation and adaptor ligation at the same time by means of the transposases, thereby reducing the time for sample preparation.

In view of the simplicity of the various operations, transposases fragmentation is undoubtedly far superior to other methods in terms of throughput and operation simplicity. However, such the fragmentation also has shortcomings. For example, transposition realized by the transposases depends on a specific 19 bp Me sequence. Therefore, though the transposases may ligate different adaptor sequences to a target sequence respectively at the 5'-terminal and the 3'-terminal by embedding two completely different adaptor sequences, the target sequence after fragmentation will symmetrically contain a Me sequence at each terminal thereof with a 9 nt gap formed between the target sequence and Me sequence due to the special function of the transposases. However, the identical Me sequences at two terminals of the target sequence will have an adverse influence on downstream technology applications. For example, when combing this adaptor ligation with the next-generation sequencing technology, the fact that the Me sequences located at two ends of the same strand of the target sequence are complementary to each other, will easily result in internal annealing within one single-stranded molecule, thus adversely contributing to combination with an anchoring primer.

There are few patents or other literatures so far reporting any molecular biology experimental method, which can extreme quickly and efficiently fragment a target sequence with transposases and correct the fragmented sequence to contain two completely different sequences at two terminal thereof.

SUMMARY

The present disclosure provides a method and reagent for constructing a library containing single-stranded cyclic nucleic acids by transposases fragmentation and constrained nick translation, by which the library containing single-stranded cyclic nucleic acids is constructed easily and quickly.

According to embodiments of a first aspect of the present disclosure, a method for constructing a library containing single-stranded cyclic nucleic acids is provided, the method includes:

randomly fragmenting a double-stranded nucleic acid sample with a transposase embedded complex, which includes transposases and a first adaptor containing a transposase recognition sequence, to obtain fragmented double-stranded nucleic acids ligated with the first adaptor at each terminal thereof; with a gap between each 3'-end and the first adaptor;

ligating a second adaptor to the fragmented double-stranded nucleic acid with ligases at the gap after removing the transposases from reaction system, the second adaptor having a sequence different from that of the first adaptor;

performing a first PCR reaction with a first primer containing a U (uracil) base to obtain a first per product ligated with a first adaptor sequence and a second adaptor sequence respectively at two ends thereof; enzyme-digesting the first per product with User (Uracil-Specific Excision Reagent) enzyme at the U base site to generate a nick, followed by double-stranded cyclization, resulting in double-stranded cyclic nucleic acids;

subjecting the double-stranded cyclic nucleic acid, as a template, to constrained nick translation from the nick;

removing a portion without occurring the constrained nick translation in the double-stranded cyclic nucleic acids by digestion to obtain double-stranded linear nucleic acids;

ligating a third adaptor and an oligonucleotide adaptor sequence to the 3'-end and the 5'-end of each strand of the double-stranded linear nucleic acid, respectively;

performing a second PCR reaction with a second primer containing a first affinity marker at the 5'-end thereof, to obtain a second per product ligated with a third adaptor sequence and the oligonucleotide adaptor sequence respectively at two ends thereof;

capturing the second per product with a carrier having a second affinity marker capable of combining with the first affinity marker, and isolating single-stranded nucleic acids without the first affinity marker through nucleic acid denaturation; and cyclizing the single-stranded nucleic acid with a single-stranded cyclization "bridge" sequence which is capable of combining with two ends of the single-stranded nucleic acid.

In embodiments of the present disclosure, the method further includes: digesting uncyclized single-stranded nucleic acids subsequent to cyclizing the single-stranded nucleic acid with the single-stranded cyclization "bridge" sequence.

In embodiments of the present disclosure, the transposase is removed from reaction system by magnetic beads purification, column purification or chemical reagent treatment.

In embodiments of the present disclosure, a length of fragment generated during the constrained nick translation is controlled by an amount of dNTPs in reaction system.

In embodiments of the present disclosure, the method further includes: digesting uncyclized first per product prior to the constrained nick translation.

In embodiments of the present disclosure, removing a portion without occurring the constrained nick translation in the double-stranded cyclic nucleic acids by digestion further includes:

digesting the double-stranded cyclic nucleic acids with double-stranded exonucleases until a first gap between two ends of the internal strand encounters a second gap between two ends of the external strand within one double-stranded cyclic nucleic acid, followed by digesting a portion without occurring the constrained nick translation in each strand of thus obtained double-stranded cyclic nucleic acids with single-stranded exonucleases.

In embodiments of the present disclosure, the method further includes: end-repairing the double-stranded linear nucleic acid and dephosphorylating the 5'-end of each strand of the double-stranded linear nucleic acid prior to ligating the third adaptor to the 3'-end of each strand of the double-stranded linear nucleic acid.

In embodiments of the present disclosure, the method further includes: subjecting dephosphorylated 5'-end of each strand of the double-stranded linear nucleic acid to phosphorylation subsequent to ligating the third adaptor to the 3'-end of each strand of the double-stranded linear nucleic acid; and ligating the oligonucleotide adaptor sequence to phosphorylated 5'-end of each strand of the double-stranded linear nucleic acid.

In embodiments of the present disclosure, the oligonucleotide adaptor sequence has a portion complementary with the third adaptor, wherein the portion is adjacent to the double-stranded linear nucleic acid.

In embodiments of the present disclosure, the first affinity marker is a biotin marker, and the second affinity marker is a streptavidin marker.

According to embodiments of a second aspect of the present disclosure, a reagent for constructing a library containing single-stranded cyclic nucleic acids is provided. The reagent includes:

a transposase embedded complex, formed with transposases and a first adaptor containing a transposase recognition sequence, and suitable for randomly fragmenting a double-stranded nucleic acid sample, to obtain fragmented double-stranded nucleic acids ligated with the first adaptor at each terminal thereof, with a gap between each 3'-end and the first adaptor;

a first component, including a second adaptor and ligases, and suitable for ligating the second adaptor to the fragmented double-stranded nucleic acid with ligases at the gap;

a first primer containing a U base, suitable to be used in a first PCR reaction to obtain a first per product ligated with a first adaptor sequence and a second adaptor sequence respectively at two ends thereof;

User enzymes, suitable for enzyme-digesting the first per product at a U base site to generate a nick, followed by double-stranded cyclization resulting in double-stranded cyclic nucleic acids;

a second component for constrained nick translation, suitable for subjecting the double-stranded cyclic nucleic acid, as a template, to constrained nick translation from the nick;

digestive enzymes, suitable for removing a portion without occurring the constrained nick translation in the double-stranded cyclic nucleic acids by digestion to obtain double-stranded linear nucleic acids;

a third adaptor, suitable for being ligated to the 3'-end of each strand of the double-stranded linear nucleic acid;

an oligonucleotide adaptor sequence, suitable for being ligated to the 5'-end of each strand of the double-stranded linear nucleic acid;

a second primer, containing a first affinity marker at the 5'-end thereof, and suitable to be used in a second PCR reaction to obtain a second per product ligated with a third adaptor sequence and the oligonucleotide adaptor sequence respectively at two ends thereof;

a carrier having a second affinity marker, suitable for capturing the second per product through combination between the first affinity marker and the second affinity marker, and isolating single-stranded nucleic acids without the first affinity marker through nucleic acid denaturation; and a single-stranded cyclization "bridge" sequence, capable of combining with two ends of the single-stranded nucleic acid, and suitable for cyclizing the single-stranded nucleic acid.

In embodiments of the present disclosure, the digestive enzymes include double-stranded exonucleases and single-stranded exonucleases.

In embodiments of the present disclosure, the reagent further includes:

an end-repairing component, suitable for end-repairing the double-stranded linear nucleic acid; and a dephosphorylation component, suitable for dephosphorylating the 5'-end of each strand of the double-stranded linear nucleic acid.

In embodiments of the present disclosure, the reagent further includes: polynucleotide kinases, suitable for subjecting dephosphoiylated 5'-end of each strand of the double-stranded linear nucleic acid to phosphorylation subsequent to ligating the third adaptor to the 3'-end of each strand of the double-stranded linear nucleic acid.

In embodiments of the present disclosure, the first affinity marker is a biotin marker, and the second affinity marker is a streptavidin marker.

With the method for constructing the library containing single-stranded cyclic nucleic acids according to the present disclosure, each target sequence fragmented by transposases will contain different adaptor sequence information at each terminals thereof by ligating a second adaptor, such that applications of fragmented target sequence is no longer restricted by the same transposase recognition sequence at two terminals thereof.

Enzyme-digestion with User enzyme and double-stranded cyclization are beneficial from the previous PCR amplification with a primer containing a U base. Following the double-stranded cyclization, a fragment with a required length can be constructed by the constrained nick translation, so that the length may be controlled in a more flexible way. Then the third adaptor and the oligonucleotide sequence are ligated, and the required single-stranded nucleic acids, isolated with affinity magnetic beads, are cyclized to obtain the library containing single-stranded cyclic nucleic acids. The whole process of the library construction is simple, easy to operate and less time spent.

DETAILED DESCRIPTION

The present disclosure will be described in further detail with reference to specific embodiments. The techniques used in embodiments below are conventional techniques known to those skilled in the art, unless specified otherwise. The instruments, equipment and reagents used herein are available to those skilled in the art through common ways, such as commercial purchase and so on.

Terms used herein are explained as follows: in specific embodiments, the first adaptor is referred to as adaptor No. 1, the second adaptor is referred to as adaptor No. 2, and the third adaptor is referred as adaptor No. 3

In present disclosure, concepts such as "first" and "second" are used in any case only for purposes of distinguishing one from other subjects, and are not intended to indicate or imply relative sequence or technique.

Figure 1:
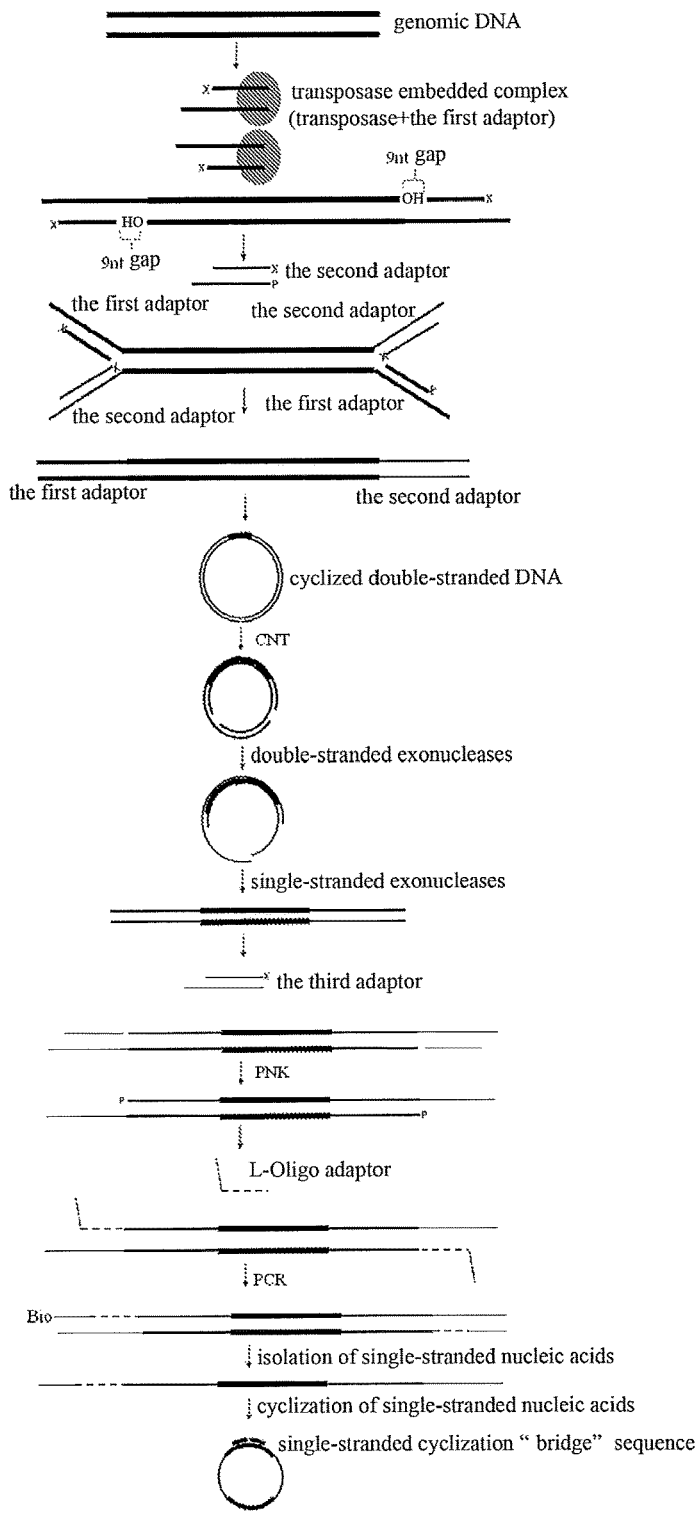
FIG. 1 is a flow chart showing a method for constructing a library containing single-stranded cyclic nucleic acids according to an embodiment of the present disclosure.

With reference to FIG. 1, the method for constructing the library containing single-stranded cyclic nucleic acids according to an embodiment of the present disclosure includes:

randomly fragmenting a double-stranded nucleic acid sample with a transposase embedded complex, which includes transposases and a first adaptor containing a transposase recognition sequence, to obtain fragmented double-stranded nucleic acids ligated with the first adaptor at each terminal thereof, with a gap (9 nt) between each 3'-end and the first adaptor;

ligating a second adaptor to the fragmented double-stranded nucleic acid with ligases at the gap after removing the transposases from reaction system, the second adaptor having a sequence different from that of the first adaptor;

performing a first PCR reaction with a first primer containing a U base to obtain a first per product ligated with a first adaptor sequence and a second adaptor sequence respectively at two ends thereof;

enzyme-digesting the first per product with User enzyme at the U base site to generate a nick, followed by double-stranded cyclization resulting in double-stranded cyclic nucleic acids;

subjecting the double-stranded cyclic nucleic acid, as a template, to constrained nick translation (CNT) from the nick;

removing a portion without occurring the constrained nick translation in the double-stranded cyclic nucleic acids by digestion with double-stranded exonucleases and single-stranded exonucleases in turn, to obtain double-stranded linear nucleic acids;

ligating a third adaptor to the 3'-end of each strand of the double-stranded linear nucleic acid, followed by subjecting the 5'-end of each strand of the double-stranded linear nucleic acid to phosphorylation with polynucleotide kinases (PNK), and ligating an oligonucleotide adaptor sequence (L-Oligo sequence) to phosphorylated 5'-end of each strand of the double-stranded linear nucleic acid;

performing a second PCR reaction with a second primer containing a first affinity marker (biotin) at the 5'-end thereof, to obtain a second per product ligated with a third adaptor sequence and the oligonucleotide adaptor sequence respectively at two ends thereof;

capturing the second per product with a carrier having a second affinity marker (streptavidin), and isolating single-stranded nucleic acids without the first affinity marker through nucleic acid denaturation; and cyclizing the single-stranded nucleic acid with a single-stranded cyclization "bridge" sequence which is capable of combining with two ends of the single-stranded nucleic acid.

In the present disclosure, the first adaptor contains the transposase recognition sequence, typically the well-known 19 bp Me sequence, and are present in double-stranded form, one strand of which may include a dideoxy modification (i.e dideoxynucleotide) at the 3'-end thereof to avoid self-ligation or inter-ligation. "Self-ligation" refers to such a ligation occurred between two adaptors in the same type, such as a ligation between two first adaptors or a ligation between two second adaptors. "Inter-ligation" refers to such a ligation occurred between two adaptors in different types, such as a ligation between the first and second adaptors. The double-stranded nucleic acid sample is fragmented by the transposase embedded complex, after which a strand of the first adaptor is ligated to a strand of the fragmented double-stranded nucleic acid, while between the other strand of the first adaptor and the other strand of the fragmented double-stranded nucleic acid, a gap in 9 nt is formed, which needs to be filled by the nick translation in a conventional method, whereas just provides a ligation site for the second adaptor in the method of the present disclosure.

In the present disclosure, the sequence of the second adaptor may be any one different from that of the first adaptor, as the second adaptor used in the present disclosure is mainly to avoid the identical transposase recognition sequence located at two ends of the double-stranded nucleic acid. After the second, adaptor is ligated at the gap, the first per product, ligated with the first adaptor sequence and the second adaptor sequence respectively at two ends thereof, may be obtained by performing the first PCR reaction with primers respectively targeting the first and second adaptors.

In the present disclosure, after fragmenting the double-stranded nucleic acid sample, the transposases are required to be removed from the reaction system generally by magnetic beads purification, column purification or chemical reagent treatment to eliminate their effects on the subsequent enzymatic reactions. The magnetic beads purification with such as Ampure XP beads and the column purification with such as purification columns form QIAGEN PCR are traditional purification methods, which are well-known in the related art. Undoubtedly, any similar product for magnetic beads purification and column purification may be used in the present disclosure. The purification can completely remove transposases from the reaction system, but will increase the corresponding operations and cost. The transposases can be dissociated from the target sequences through denaturation or digestion by the chemical reagent treatment due to their protein nature, and have lost their biological activities after above treatment, thus will not have a negative impact on the subsequent reaction, even may still remain in the system.

In the present disclosure, during the chemical reagent treatment, protease solution, sodium dodecyl sulfate (SDS) solution, NT buffer (NT buffer included in Truprep kit in S5 series) and the like may be firstly chosen to break the adsorption between the transposase and the target sequence of nucleic acid, followed by purification treatment.

In the present disclosure, a length of fragment generated during the constrained nick translation is controlled by an amount of dNTPs in reaction system, as the constrained nick translation will stop when dNTPs, raw material of constrained nick translation, are exhausted. Therefore, the amount of dNTPs is a critical restrictive factor in the present disclosure, which may be determined by the desired fragment length. This allows for the generation of fragments in specific lengths required by the specific library for the specific sequencing platform, without tedious steps of fragment selections, such as gel extraction, in the later stage.

In the present disclosure, the constrained nick translation is performed taking the double-stranded cyclic nucleic acid as a template. Therefore, the uncyclized first per product is required to be digested prior to the constrained nick translation to eliminate their impact on the constrained nick translation. In an embodiment of the present disclosure, exonucleases are used to digest the uncyclized first per product.

In the present disclosure, subsequent to the constrained nick translation, a portion without occurring the constrained nick translation in the double-stranded cyclic nucleic acids is removed by digestion respectively with double-stranded exonucleases and single-stranded exonucleases to obtain double-stranded linear nucleic acids. However, the double-stranded linear nucleic acids thus obtained further needs to be end-repaired with polymerases due to their possible unblunt ends. Moreover, in order to avoid the self-ligation, the 5'-end of each strand of the double-stranded linear nucleic acid is required to be dephosphorylated.

In the present disclosure, as the third adaptor and the oligonucleotide adaptor sequence are ligated to the 3'-end and the 5'-end of each strand of the double-stranded linear nucleic acid, respectively, the third adaptor is subjected to dideoxy modification at the 3'-end of one strand thereof (i.e. the 3'-end of one strand of the third adaptor is dideoxynucleotide) to ensure that only the 5'-end of the other strand of the third adaptor is ligated to the 3'-end of each strand of the double-stranded linear nucleic acid. The dephosphorylated 5'-end of each strand of the double-stranded linear nucleic acid is required to be phosphorylated with polynucleotide kinases so as to ligate the oligonucleotide adaptor sequence after the third adaptor is ligated to the 3'-end of each strand of the double-stranded linear nucleic acid.

In the present disclosure, the difference between the oligonucleotide adaptor sequence and any one of the first adaptor, the second adaptor and the third adaptor lies in that the oligonucleotide adaptor sequence is a single-stranded nucleotide sequence, while the first adaptor, the second adaptor and the third adaptor all are doubled-stranded nucleotide sequences. The 3'-end of oligonucleotide adaptor sequence is ligated to the phosphorylated 5'-end of each strand of the double-stranded linear nucleic acid. In an embodiment of the present disclosure, the oligonucleotide adaptor sequence has a portion complementary with the third adaptor by which the oligonucleotide adaptor sequence may be positioned at the ligation site, thus improving the ligation efficiency, wherein the portion is adjacent to the double-stranded linear nucleic acid, moreover, as other bases of the oligonucleotide adaptor sequence are not complementary with the third adaptor, a product ligated with different sequences respectively at two ends thereof may be obtained through a specific PCR amplification after the oligonucleotide adaptor sequence is ligated, thus avoiding the adverse effects brought by the same sequence at two ends of the product.

In the present disclosure, one of a pair of primers used in the second PCR contains a first affinity marker at the 5'-end thereof, and the first affinity maker may be a component commonly used in biological binding reactions, such as an antigen or antibody, a strand of short double-stranded DNA fragment, biotin or streptavidin, and so on. In the case where the antigen is selected as the first affinity marker, the antibody which is capable of binding to the antigen is selected as the second affinity marker, and vice versa. In the case where one strand of short double-stranded DNA fragment is selected as the first affinity marker, the other complementary strand of the same short double-stranded DNA fragment is selected as the second affinity marker, and vice versa. In the case where the biotin is selected as the first affinity marker, the streptavidin which is capable of binding to the biotin is selected as the second affinity marker, and vice versa. In an embodiment of the present disclosure, the first affinity marker is biotin, and the second affinity marker is streptavidin, both of which have a strong binding capacity.

In the present disclosure, the carrier for capturing the second per product may be a chip or magnetic beads. Specifically, the chip or magnetic beads is coated with the second affinity marker which is capable of combining with the first affinity marker. In an embodiment of the present disclosure, the magnetic beads coated with the streptavidin marker are used.

In the present disclosure, the second per product captured by the carrier may be denatured by heat or alkali, preferably alkali, such as sodium hydroxide or potassium hydroxide. In an embodiment of the present disclosure, sodium hydroxide is used.

In the present disclosure, the single-stranded cyclization "bridge" sequence is such a sequence that is complementary with two ends of the single-stranded nucleic acid and thus bridges the two ends of the single-stranded nucleic acid, so as to achieve the cyclization of the single-stranded nucleic acid.

In the followings, the present disclosure will be described in detail with reference to embodiments.

In the present embodiment, a transposases kit (Vazyme Biotech) was used for technology development, which included genomic DNA in two amounts, 5 ng and 50 ng, the latter was chosen in the present embodiment.

In the present embodiment, an embedded adaptor sequence (Adaptor No. 1) was independently designed, and a transposase embedded complex was prepared using the transposases and the embedded adaptor sequence, furthermore, a new method for constructing a library was achieved by combining the transposases operation with CNT. The detail operation steps of the present embodiment were as follows:

1. A pair of primer sequences (sequence A and sequence B) containing 19 bp Me sequence was designed and purchased for the preparation of a single-ended adaptor (Adaptor No. 1) for embedding:

Sequence A of adaptor No. 1: AGGUCGCCAGCCCUACAGATGTGTATAAGAGACAG (SEQ ID NO:1);

Sequence B of adaptor No. 1: CTGTCTCTTATACACATC ddT (SEQ ID NO:2, dd represents a dideoxy modification at the 3'-end).

Adaptor No. 2 (sequence A and sequence B) for ligation was designed and purchased:

Sequence A of adaptor No. 2:
pACTGCTGAGCTGAGGANNNNNNNNNTCGTCAAGGTCGCCAGCC ddC (SEQ ID NO:3, dd represents the dideoxy modification at the 3'-end, p represents a phosphorylation modification at the 5'-end, N represents a tag sequence for distinguishing different samples);

Sequence B of adaptor No. 2: TCCTCAGCTCAGCAG ddT (SEQ ID NO:4, dd represents the dideoxy modification at the 3'-end).

2. The sequence A and sequence B of the adaptor No. 1 were diluted to 100 μM, centrifuged after sufficiently mixed, and then annealed in the PCR apparatus according to the following procedures (Table 1) to obtain adaptor No. 1, which was stored at −20° C. for the preparation of the transposase embedded complex.

TABLE 1

| temperature | time |
| --- | --- |
| 75° C. | 15 min |
| 60° C. | 10 min |
| 50° C. | 10 min |
| 40° C. | 10 min |
| 25° C. | 30 min | hot lid 105° C.

3. The components shown in the following system (Table 2) was mixed by gently blowing up and down for 20 times and then incubated at 30° C. for 1 hour to embed the adaptor No. 1 into transposases, thus obtaining the transposase embedded complex, which was stored at −20° C.

TABLE 2

| Component | Amount |
| --- | --- |
| Transposase | 85 μl |
| Adaptor No. 1 | 30 μl |
| Coupling buffer | 85 μl |
| Total | 200 μl |

4. 50 ng genomic DNA with high quality was mixed with the transposase embedded complex together with other components shown in Table 3 by gently blowing up and down for 20 times, followed by incubation at 55° C. for 10 min and subsequently cooling down to 4° C., such that the genomic DNA was fragmented.

TABLE 3

| Component | Amount |
| --- | --- |
| Water | 5 μL |
| 5× Fragmenting buffer | 2 μl |
| gDNA (50 ng/μL) | 1 μL |
| Transposase embedded complex | 2 μL |
| Total | 10 μL |

Fragmented genomes obtained above were firstly mixed with 2.5 μL of 0.5% SDS to be uniform, then purified and recovered with Ampure XP beads in 1.2 folds and redissolved with water or TE to obtain a fragmented and purified product.

5. The fragmented and purified product was incubated with other components shown in Table 4 at 25° C. for 60 min to achieve the ligation of the adaptor No. 2, followed by purifying with Ampure XP beads in 1.2 folds and re-dissolved with pure water.

TABLE 4

| Component | Amount |
| --- | --- |
| Water | 8 μl |
| 3× Ligation buffer | 20 μL |
| Adaptor No. 2 (5 μM) | 10 μL |
| Ligases | 2 μL |
| DNA | 20 μL |
| Total | 30 μL |

6. The PCR amplification was performed in accordance with the following system (Table 5) and reaction conditions (Table 6) to obtain the first PCR product.

TABLE 5

| Component | Amount |
| --- | --- |
| DNA | 21.3 μL |
| 5× PCR mix buffer | 25 μL |
| Primer 1 | 1.25 μL |
| Primer 2 | 1.25 μL |
| PCR enzyme | 1.2 μL |
| Total | 50 μL |

Where the sequences of the PCR primers were as follow:

```
                                        (SEQ ID NO: 5)
Primer 1:   AGGUCGCCAGCCCUACAGATGTGTATAAGAGACAG;

(SEQ ID NO: 6)
Primer 2:   GGGCUGGCGACCTUGACGA.
```

TABLE 6

| Temperature | Time | cycle |
| --- | --- | --- |
| 95° C. | 3 min | 1 cycle |
| 95° C. | 30 sec | |
| 60° C. | 30 sec | 9 cycles |
| 72° C. | 3 min | |
| 68° C. | 10 min | 1 cycle |
| 4° C. | ∞ | — |

7. User enzyme reaction system (Table 7) was prepared and then mixed with the first PCR product to obtain a mixture, which was incubated in PCR apparatus at 37° C. for 1 hour, followed by gradually dropping the temperature to 4° C.

TABLE 7

| Component | Amount |
| --- | --- |
| Pure water | 25.8 μl |
| User enzyme buffer | 11 μL |
| User enzyme | 13.2 μL |
| Total | 50 μl |

8. Double-stranded cyclization: An enzyme reaction mixture was prepared as follows (Table 8):

TABLE 8

| Component | Amount |
| --- | --- |
| Pure water | 1520 μl |
| 10× TA reaction buffer (EPICENTRE BIOTECHNOLOGIES Company, Item No.: TA6160) | 180 μL |
| Total | 1700 μL |

The product obtained in the previous step was evenly distributed into four small tubes with 27.5 μL for each tube, to each of which 423 μL of the above enzyme reaction mixture was added. After shaken, the newly obtained mixture in each tube was incubated in a water bath at 70° C. for 30 min, then cooled in another water bath at room temperature for 20 min, to which 50 μL of enzyme reaction mixture for cyclization, prepared according to Table 9, was added to carry out the cyclization at room temperature for 1 hour. After the reaction, the obtaining product was purified with Ampure XP beads in o.6 fold in volume, and the resulting supernatant was purified and recovered with additional Ampure XP beads in o.4 fold in volume, followed by dissolved in water or TE.

TABLE 9

| Component | Amount |
| --- | --- |
| Pure water | 98 μl |
| Cyclization buffer | 100 μL |
| T4 DNA ligases (Enzymatics Company, Item No.: L6030-LC-L) | 2 μL |
| Total | 200 μL |

9. 60 μL of purified DNA sample was added with 20 μL of the following enzyme reaction solution (Table 10) for digesting uncyclized DNAs, then incubated at 37° C. for 1 hour and then gradually cooled to 4° C.

TABLE 10

| Component | Amount |
| --- | --- |
| Pure water | 0.7 μl |
| Digestive enzyme buffer | 8.9 μL |
| Digestive enzyme (Plasmid-Safe ATP-Dependent Dnase, EPICENTRE BIOTECHNOLOGIES Company, Item No.: E3110K) | 10.4 μL |
| Total | 20 μL |

After digestion, the purification was performed with Ampure XP beads in 1 fold in volume, and recovery was performed with pure water or TE.

10. The following mixture (Table 11) was prepared, which was suitable to be used in CNT reaction to generate DNA product in a suitable length.

TABLE 11

| | |
| --- | --- |
| Pure water | 5.6 μL |
| Dilute dNTP | 3.9 μL |
| NEB buffer 2 | 5.5 μL |
| DNA | 40 μL |
| Dilute polymerase | 5 μL |
| Total | 60 μL |

The dilute dNTP was prepared as follows: 2 μL 25 mM dNTP was evenly mixed with 18 μL pure water to obtain 20 μL, 2.5 mM dNTP, from which 3 μL dNTP was taken and evenly mixed with 327 μL pure water; the dilute polymerase was prepared as follows: the polymerase was diluted with CNT buffer at 1:4.

CNT reaction was performed according to the following procedures (Table 12):

TABLE 12

| temperature | time |
| --- | --- |
| 8° C. | 15 min |
| 65° C. | 15 min |
| 4° C. | ∞ |

11. The product obtained in the previous step was added into the following reaction solution (Table 13), a mixture thus obtained was held at 25° C. for 1 hour, and then cooled to 4° C., so as to digest a partial double-strand at the gap.

TABLE 13

| Component | Amount |
| --- | --- |
| Pure water | 15.15 μL |
| NEB buffer4 | 10 μL |
| T7 exonuclease | 14.85 |
| DNA | 60 μL |
| Total | 100 μL |

After the reaction was completed, a product thus obtained was purified with PEG 32 beads in 0.6 fold in volume and re-dissolved with water or TE.

12. A reaction system for digesting single-stranded nucleic acids was prepared in according to Table 14, then incubated at 37° C. for 30 mM, followed by gradually cooled to 4° C.

TABLE 14

| Component | Amount |
| --- | --- |
| Pure water | 14.51 μl |
| Buffer of exonuclease 8 | 10 μl |
| Exonuclease 8 | 0.495 ul |
| DNA | 25 μl |
| Total | 50 μl |

After the reaction was completed, a product thus obtained was purified with Ampure XP beads in 1 fold in volume and re-dissolved with pure water or TE buffer. Concentration was detected by Qubit, and a size of obtained fragment was checked by gel electrophoresis.

13. End-repairing product obtained in previous step

The components listed in Table 15 were incubated at 12° C. for 20 min, and then cooled down to 4° C. gradually.

TABLE 15

| Component | Amount |
| --- | --- |
| End-repairing buffer | 5.4 μL |
| Deoxynucleotide | 0.8 μL |
| Bovine serum albumin | 0.4 μL |
| DNA | 44 μl |
| Polymerase | 2 μl |
| Total | 52.6 μl |

After the reaction was completed, a product thus obtained was purified and recovered with PEG 32 beads in 1.3 fold and re-dissolved with pure water or TE.

14. Dephosphorylation reaction system (Table 16) was formulated, then incubated at 37° C. for 45 min, followed by gradually cooled down to 4° C. gradually.

TABLE 16

| Component | Amount |
| --- | --- |
| Dephosphorylated buffer | 5.75 μL |
| Dephosphorylase | 5.75 μL |
| DNA | 46 μL |
| Total | 57.5 μL |

After the reaction was completed, a product thus obtained was purified and recovered with PEG 32 beads in 1.3 fold and re-dissolved with pure water or TE buffer.

15. Designation and Customization of the third adaptor:

The third adaptor sequence-1: pAAGTCGGAGGC-CAAGCGTGCTTAGGA (SEQ ID NO:7, preprensents phosphorylation modification at the 5'-end);

The third adaptor sequence-2: TCCGACT ddT (SEQ ID NO:8, dd represents dideoxy modification at the 3'-end).

The following reaction system (Table 17) was formulated to introduce the third adaptor, and incubated at 25° C. for 1 hour, followed by incubated at 65° C. for 10 min, and then gradually cooled down to 4° C.

TABLE 17

| Component | Amount |
| --- | --- |
| The third adaptor sequence | 7.5 μL |
| Ligation buffer | 24.8 μL |
| Ligases | 2.1 μl |
| DNA | 40 μL |
| Total | 74.4 μL |

After the reaction was completed, 1 μl Polynucleotide kinases were added, the system thus obtained was incubated at 37° C. for 20 min, followed by gradually cooled down to 4° C. A product thus obtained was purified with Ampure XP beads in 1 fold in volume and eluted with pure water or TE buffer.

16. Customization of the L-Oligo adaptor:

pCATGTAGTGTACGATCCGACTT (SEQ ID NO:9, p represents phosphorylation modification at the 5'-end);

The following reaction system (Table 18) was formulated to introduce the L-Oligo adaptor.

TABLE 18

| Component | Amount |
| --- | --- |
| Pure water | 5 μl |
| L-Oligo adaptor | 4 μL |
| Ligation buffer | 25 μL |
| Ligases | 1 μL |
| DNA | 40 μL |
| Total | 75 μL |

After the reaction was completed, a product thus obtained was purified and recovered with Ampure XP beads in 1.1 fold and re-dissolved with water or TE buffer.

17. The following PCR system was formulated to amplify the DNA product.

TABLE 19

| Component | Amount |
| --- | --- |
| Pure water | 136.5 μl |
| PCR buffer | 275 μL |
| PCR enzyme | 11 μL |
| Adaptor primer-1 | 13.75 μL |
| Adaptor primer-2 | 13.75 μL |
| DNA | 100 μL |
| Total | 550 μL |

550 μL of the PCR system was evenly distributed into 4 tubes with 110 μL for each tube. The PCR procedure was performed as follows (Table 20).

TABLE 20

| Temperature | Time | cycle |
| --- | --- | --- |
| 95° C. | 3 min | 1 cycle |
| 95° C. | 30 sec | 7 cycles |
| 60° C. | 30 sec | |
| 72° C. | 3 min | |
| 68° C. | 10 mm | 1 cycle |
| 4° C. | ∞ | — |

Note: adaptor primer-1: 5'Bio-TCCTAAGCACGCTTG-GCCT (SEQ ID NO:10, Bio represents a biotin modification at the 5'-end); adaptor primer-2: pCATGTAGTGTAC-GATCCGACTT (SEQ ID NO:11, p represents a phosphorylation modification at the 5'-end).

After the reaction was completed, contents contained in two tubes were taken together. A product thus obtained was purified and recovered with PEG32 beads in 1.1 fold and re-dissolved with water or TE buffer. A sample was taken for Qubit detection and electrophoresis.

18. The following reagents (Table 21 and Table 22) were formulated for isolating single-stranded nucleic acids:

TABLE 21

| 1× binding elution buffer/tween mixture | |
| --- | --- |
| Component | Amount |
| 1× binding elution buffer | 2000 μl |
| 0.5% tween 20 | 20 μL |
| Total | 2020 μL |

TABLE 22

| 0.1 mM NaOH solution | |
| --- | --- |
| Component | Amount |
| 0.5M NaOH | 15.6 µL |
| Pure water | 62.4 µL |
| Total | 78.0 µL |

4×high salinity binding buffer in 1/3-fold in volume was added into 60 µL DNA, 40 µL of beads coated with streptomycin was added into 1×high salt binding buffer, and single-stranded nucleic acids were isolated with the prepared NaoH solution, a product thus obtained was purified and recovered by washing with 1×binding elution buffer/tween mixture.

19. In accordance with the following systems (Tables 23 and 24), two ends of the isolated single-stranded nucleic acid were bridged with the single-stranded cyclization "bridge" sequence (the fourth adaptor) as a binding bridge to form the library containing single-stranded cyclic nucleic acids.

TABLE 23

| Component | Amount |
| --- | --- |
| Isolated single-stranded DNAs | 58 µL |
| The fourth adaptor | 2 µL |
| Total | 60 µL |

The system shown in Table 23 was incubated at 75° C. for 5 min, then gradually cooled down to 20° C.

Where the fourth adaptor has a sequence: GTACACTA-CATGTCCTAAGCACGC (SEQ ID NO:12).

Then the cyclization system (Table 24) was formulated, and incubated at 37° C. for 1 hour, followed by gradually cooled down to 4° C.

TABLE 24

| Component | Amount |
| --- | --- |
| Pure water | 2.1 µl |
| 10× TA reaction buffer | 7.0 µL |
| Adenosine triphosphate | 0.7 µL |
| Isolated single-stranded DNAs + the fourth adaptor | 60 µL |
| Ligases | 0.2 µL |
| Total | 70 µL |

After the reaction was completed, 10 µL of sample was taken for electrophoretic detection.

20. Enzyme-digestion reaction was performed by incubating components listed in Table 25 at 37° C. for 30 min, followed by slowly dropping the temperature to 4° C.

TABLE 25

| Component | Amount |
| --- | --- |
| Pure water | 0.35 µl |
| 10× TA reaction buffer | 0.35 µL |
| Exonuclease 1 | 2.1 µL |
| Exonuclease 3 | 0.7 µL |
| DNA | 65 µL |
| Total | 69.5 µL |

After the reaction was completed, a product thus obtained was purified and recovered with PEG 32 beads in 1.3 folds in volume, and re-dissolved with pure water or TE butter.

Figure 2:
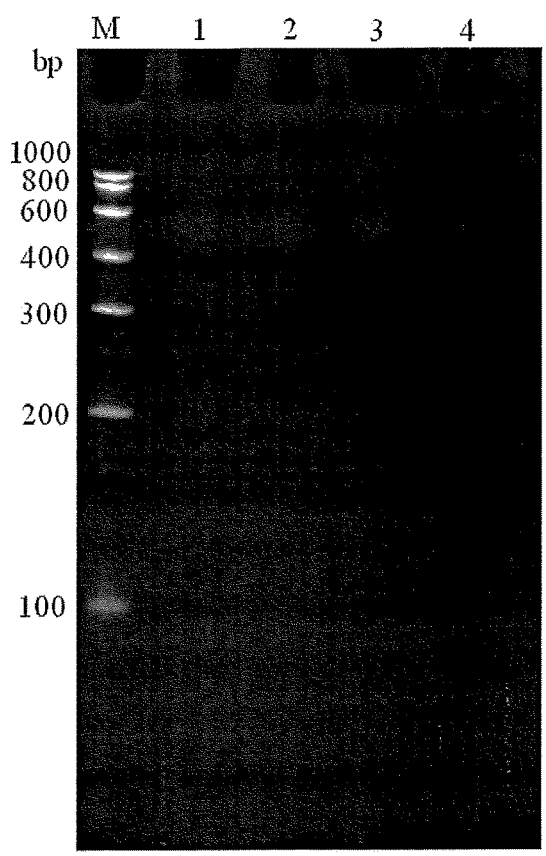
FIG. 2 is a diagram showing the result of a 6% Page Gel Electrophoresis test for the single-stranded cyclic nucleic acids prepared according to an embodiment of the present disclosure, where M represents DNA Marker, and 1, 2, 3, 4 are parallel tests of four samples.

21. Detection: 2 µL of single-stranded cyclic product after purified was taken for electrophoretic detection, and the concentration of single-stranded cyclic product in each lane was 2 ng/µL. Results shown in FIG. 2 indicated that cyclic single-strand was presented. As cyclic nucleic acids ran slower than single-stranded or double-stranded nucleic acids, so their corresponding bands distributed somewhat higher. Results of the detection to the single-stranded cyclic product after purified with Agilent 2100, shown in FIG. 3, indicates that the single-stranded cyclic product is about 236 bp, which meets the size requirement to cyclic product, thus may be used for computer sequencing.

Figures 3, 4:
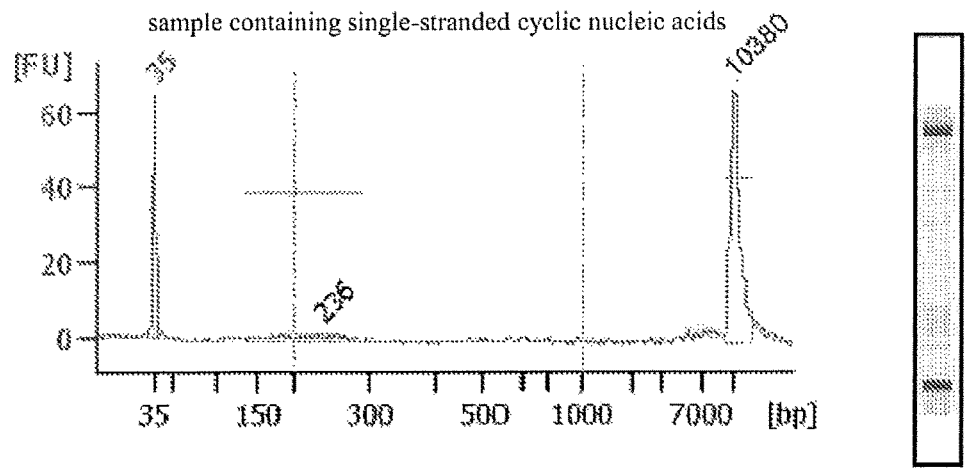
FIG. 3 is a diagram showing detection results of the single-stranded cyclic nucleic acids prepared according to an embodiment of the present disclosure by Agilent 2100.
FIG. 4 is a diagram showing base masses obtained by sequencing the single-stranded cyclic nucleic acids prepared according to an embodiment of the present disclosure.

22. Sequencing: the library containing single-stranded cyclic nucleic acids was sequenced on CG sequencing platform after it was constructed. The results of base qualities obtained from the sequencing are shown in FIG. 4, in which most data is between 80 and 90, which is higher than 75, a generally acceptable data, and such results cannot be reached by the traditional method that uses nucleic acid with 19 bp transposase recognition sequence at each end thereof, from which data obtained even is only between 30 to 40.

The above content is a further detailed description of the present disclosure in combination with the specific embodiments. However, the specific embodiments of the present disclosure shall not be limited to these instructions. It would be appreciated by those skilled in the art that some simple deductions or replacements can be made in the embodiments without departing from spirit, principles and scope of the present disclosure.

What is claimed is:

1. A method for constructing a library containing single-stranded cyclic nucleic acids, comprising:

randomly fragmenting a double-stranded nucleic acid sample with a transposase embedded complex, which comprises transposase and a first adaptor containing a transposase recognition sequence, to obtain fragmented double-stranded nucleic acids ligated with the first adaptor at each terminal thereof, with a gap between each 3'-end and the first adaptor;

ligating with a ligase a second adaptor to the fragmented double-stranded nucleic acid at the gap after removing the transposase from the reaction system, the second adaptor having a sequence different from that of the first adaptor;

performing a first PCR reaction with a first primer containing a uracil to obtain a first PCR product ligated with a first adaptor sequence and a second adaptor sequence respectively at two ends thereof;

enzyme-digesting the first PCR product with User enzyme at the uracil site to generate a gap, followed by double-stranded cyclization resulting in double-stranded cyclic nucleic acids;

subjecting the double-stranded cyclic nucleic acid, as a template, to constrained nick translation from the gap;

removing a portion without occurring the constrained nick translation in the double-stranded cyclic nucleic acids by digestion to obtain double-stranded linear nucleic acids;

ligating a third adaptor and an oligonucleotide adaptor sequence to the 3'-end and the 5'-end of each strand of the double-stranded linear nucleic acid, respectively;

performing a second PCR reaction with a second primer containing a first affinity marker at the 5'-end thereof, to obtain a second PCR product ligated with a third adaptor sequence and the oligonucleotide adaptor sequence respectively at two ends thereof;

capturing the second PCR product with a carrier having a second affinity marker capable of combining with the first affinity marker, and isolating single-stranded nucleic acids without the first affinity marker through nucleic acid denaturation; and cyclizing the single-stranded nucleic acids without the first affinity marker with a single-stranded cyclization "bridge" sequence which is capable of combining with two ends of each single-stranded nucleic acid.

2. The method according to claim 1, further comprising: digesting uncyclized single-stranded nucleic acids subsequent to cyclizing the single-stranded nucleic acids with the single-stranded cyclization "bridge" sequence.

3. The method according to claim 1, wherein the transposase is removed from the reaction system by magnetic beads purification, column purification or chemical reagent treatment.

4. The method according to claim 1, wherein a length of fragment generated during the constrained nick translation is controlled by an amount of dNTPs in the reaction system.

5. The method according to claim 1, further comprising digesting uncyclized first PCR product prior to the constrained nick translation.

6. The method according to claim 1, wherein removing a portion without occurring the constrained nick translation in the double-stranded cyclic nucleic acids by digestion further comprises:

digesting the double-stranded cyclic nucleic acids with a double-stranded exonuclease until a first gap between two ends of the internal strand encounters a second gap between two ends of the external strand within one double-stranded cyclic nucleic acid; followed by digesting a portion without occurring the constrained nick translation in each strand of thus obtained double-stranded cyclic nucleic acids with a single-stranded exonuclease.

7. The method according to claim 1, further comprising:
end-repairing the double-stranded linear nucleic acid and dephosphorylating the 5'-end of each strand of the double-stranded linear nucleic acid prior to ligating the third adaptor to the 3'-end of each strand of the double-stranded linear nucleic acid.

8. The method according to claim 7, comprising:
subjecting the dephosphorylated 5'-end of each strand of the double-stranded linear nucleic acid to phosphorylation subsequent to ligating the third adaptor to the 3'-end of each strand of the double-stranded linear nucleic acid; and
ligating the oligonucleotide adaptor sequence to the phosphorylated 5'-end of each strand of the double-stranded linear nucleic acid.

9. The method according to claim 1, wherein the oligonucleotide adaptor sequence has a portion complementary with the third adaptor, wherein the portion is adjacent to the double-stranded linear nucleic acid.

10. The method according to claim 1, wherein the first affinity marker is a biotin marker, and the second affinity marker is a streptavidin marker.

* * * * *